US006768036B2

(12) United States Patent
Lattner et al.

(10) Patent No.: US 6,768,036 B2
(45) Date of Patent: Jul. 27, 2004

(54) METHOD FOR ADDING HEAT TO A REACTOR SYSTEM USED TO CONVERT OXYGENATES TO OLEFINS

(75) Inventors: James R. Lattner, Seabrook, TX (US); Keith H. Kuechler, Friendswood, TX (US); Richard E. Walter, Long Valley, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 10/422,924

(22) Filed: Apr. 24, 2003

(65) Prior Publication Data

US 2003/0199720 A1 Oct. 23, 2003

Related U.S. Application Data

(63) Continuation-in-part of application No. 10/152,908, filed on May 22, 2002
(60) Provisional application No. 60/345,681, filed on Dec. 31, 2001.

(51) Int. Cl.[7] .................................................. C07C 1/00
(52) U.S. Cl. ...................................... 585/639; 585/640
(58) Field of Search ................................. 585/639, 640

(56) References Cited

U.S. PATENT DOCUMENTS

| 4,595,567 A | 6/1986 | Hedrick ....................... 422/146 |
| 4,615,992 A | 10/1986 | Murphy ....................... 502/41 |
| 4,939,314 A | 7/1990 | Harandi et al. ............. 585/533 |
| 6,023,005 A | 2/2000 | Lattner et al. .............. 585/639 |
| 6,166,282 A | 12/2000 | Miller ......................... 585/638 |

FOREIGN PATENT DOCUMENTS

GB             602263        5/1948

Primary Examiner—Thuan D Dang (57) ABSTRACT

The present invention provides a method for adding heat to a reactor system used to convert oxygenates to olefin, in which supplemental heat is added with a heating fuel, e.g., a torch oil, having low autoignition temperature, low sulfur, and low nitrogen content.

41 Claims, 1 Drawing Sheet

METHOD FOR ADDING HEAT TO A REACTOR SYSTEM USED TO CONVERT OXYGENATES TO OLEFINS

REFERENCE TO RELATED APPLICATIONS

This application is a continuation-in-part of U.S. application Ser. No. 10/152,908 filed May 22, 2002 which claims the benefit of No. 60/345,681, filed Dec. 31, 2001, the entire content of these applications are incorporated herein by reference.

FIELD OF THE INVENTION

The present invention relates to a method for converting a feed including an oxygenate to a product including a light olefin, in which supplemental heat is added with a heating fuel having low autoignition temperature, low sulfur, and low nitrogen content.

BACKGROUND OF THE INVENTION

Light olefins, defined herein as ethylene, propylene, butylene and mixtures thereof, serve as feeds for the production of numerous important chemicals and polymers. Particularly, light olefins are used in the manufacture of polyolefins such as polypropylene and polyethylene. Catalysts for polyethylene and polypropylene require a product that is substantially free of contaminants such as sulfur and nitrogen. When sulfur and nitrogen compounds are present in the olefin feedstock, the catalyst is rendered less effective resulting in poorer quality goods or less efficient polymerization products.

One emerging technology for the production of light olefins uses oxygenate feedstocks such as methanol, ethanol or dimethyl ether. Methanol, ethanol and dimethyl ether feedstocks are produced from synthesis gas derived from natural gas or other sources. Oxygenate feedstocks produced from this method are desirable because they contain negligible amounts of nitrogen or sulfur and result in olefin products that are less poisonous to polymerization catalysts. One embodiment of the reaction of oxygenates to olefins uses a molecular sieve catalyst, such as a SAPO catalyst, in a reactor system that has an oxygenate to olefin ("OTO") reactor and a catalyst regenerator. The catalyst in the OTO reactor converts oxygenates to olefins and also generates and deposits carbonaceous material (coke) on the molecular sieve catalysts used to catalyze the conversion process. Over accumulation of these carbonaceous deposits will interfere with the catalyst's ability to promote the reaction. Thus, the molecular sieve catalyst is periodically recycled to the catalyst regenerator. During regeneration, the coke is removed from the catalyst by combustion with oxygen, which restores the catalytic activity of the catalyst. The regenerated catalyst is then recycled back to the OTO reactor where it is reused to catalyze the OTO reaction.

U.S. Pat. Nos. 6,023,005 and 6,166,282, both of which are incorporated herein by reference, disclose methods of producing ethylene and propylene by catalytic conversion of oxygenate in a fluidized bed reaction process which utilizes catalyst regeneration.

U.S. Pat. Nos. 4,595,567, and 4,615,992, both of which are incorporated herein by reference, disclose general and specific regeneration devices and techniques.

The reactor system comprising an OTO reactor and a regenerator often requires the addition of heat to the reactor system. The OTO reaction is exothermic, requiring an initial heating to initiate the reaction, after which it is self-sustaining. There are also periods where the oxygenate feed must be interrupted, at which time it would be desirable to keep the reactor and regenerator hot. In addition, the initial start-up of the regenerator and heating of the catalyst also requires heat.

Conventionally, the regenerator apparatus is preheated by an auxiliary burner which burns a starting fuel such as natural gas with air to provide a heated gas that contains air and gaseous combustion products such as carbon dioxide and water (steam), to the regenerator. The auxiliary burner can be associated with the regenerator air blower that introduces the heated gas through an air inlet at the bottom of the regenerator. However, given the low heat capacity of such heated gas, resulting in part from its expansion upon heating, the heat input to the unit is limited. Particularly, the maximum amount of heat and the maximum temperature is limited. When heat is added to reactors other than OTO reactor systems, such as a fluid catalytic cracking (FCC) system, hydrocarbon feed (gas oil) to the FCC unit is burned in the regenerator to heat the catalyst. However, the gas oil feedstock of an FCC unit is contaminated with nitrogen and sulfur and would be unsuitable in an OTO process, as the gas oil would increase the levels of these contaminants in the products. Methanol is undesirable as a fuel for heating catalyst because it has a high autoignition temperature, and igniting and sustaining the burning of methanol would be difficult. The process of fluid catalytic cracking (FCC) normally circulates hot catalyst from the regenerator to the reactor to add heat to the reactor. One method of doing this combusts a fuel with the air feed to the regenerator. The FCC process normally uses fuel gas (including natural gas), or a combination of fuel gas and heavy liquid feedstock for this purpose. The fuel gas is combusted in an auxiliary burner, located after the air blower but before entering the fluidized bed of catalyst in the regenerator. The limited heat capacity of the regeneration air, resulting in part from its expansion upon heating, limits the rate at which heat is added to the regenerator through this method. It is normally desirable to add heat at a greater rate, and thus a liquid fuel, normally consisting of gas oil feedstock, is added to the fluidized catalyst zone. The catalyst has a much higher heat capacity than the combustion air, and thus liquid fuel can be added at a much greater rate in the fluidized catalyst zone than can be added to the combustion air through the auxiliary burner. The gas oil also has a relatively low autoignition temperature of 315–370° C. (600–700° F.), which aids in the initiation of combustion, as well as helping to ensure that the combustion will not be extinguished during a low temperature excursion.

In trying to adapt the FCC heating method to the MTO process, some major problems are encountered. Gas oil cannot be used as the heating fuel, because the sulfur and nitrogen introduced by the gas oil cannot be tolerated in the MTO product recovery section. The MTO feedstock, methanol, cannot be used as the heating fuel, because its autoignition temperature of 468° C. (875° F.) is so high that preheating the catalyst bed in the regenerator to a sufficient temperature to initiate the combustion of methanol is difficult. Also, there is a greater risk of extinguishing the burn from a low temperature excursion.

Accordingly, it would be desirable to provide a process for making olefins from oxygenate which has an initiation procedure which provides a high heat input to an oxygenate to olefins reactor system within a reasonable time, hours rather than days, to provide supplemental heat to the reactor, without contaminating either the OTO catalyst or the MTO products and byproducts. The present invention satisfies these and other needs.

SUMMARY OF THE INVENTION

The present invention solves the current needs in the art by providing a method for converting a feed including an oxygenate to a product including a light olefin.

The method of the present invention is conducted in a reactor apparatus. As used herein, the term "reactor apparatus" refers to an apparatus which includes at least a place in which an oxygenate to olefin conversion reaction takes place. As further used herein, the term "reaction zone" refers to the portion of a reactor apparatus in which the oxygenate to olefin conversion reaction takes place and is used synonymously with the term "reactor." Desirably, the reactor apparatus includes a reaction zone, an inlet zone and a disengaging zone. The "inlet zone" is the portion of the reactor apparatus into which feed and catalyst are introduced. The "reaction zone" is the portion of the reactor apparatus in which the feed is contacted with the catalyst under conditions effective to convert the oxygenate portion of the feed into a light olefin product. The "disengaging zone" is the portion of the reactor apparatus in which the catalyst and any additional solids in the reactor are separated from the products. Typically, the reaction zone is positioned between the inlet zone and the disengaging zone.

The present invention relates to a process for making an olefin product from an oxygenate feedstock in the presence of an oxygenate to olefin molecular sieve catalyst which comprises:
  a) contacting at least a portion of the catalyst with a regeneration medium in a regeneration zone;
  b) heating said regeneration zone to a first temperature of at least 225° C. (437° F.), e.g., at least 260° C. (500° F.),
  c) feeding to said regeneration zone a heating fuel having an autoignition temperature less than the first temperature and containing less than 500 wppm sulfur, e.g., less than 100 wppm sulfur, and less than 200 wppm nitrogen, e.g., less than 100 wppm nitrogen, thereby causing the heating fuel to ignite and provide a heated catalyst; and
  d) circulating said heated catalyst to the reaction zone; and
  e) additionally contacting the feedstock in a reaction zone with said oxygenate to olefin molecular sieve catalyst including said heated catalyst, under conditions effective to convert the feedstock into an olefin product stream.

In one embodiment, the olefin product stream comprises $C_2$–$C_3$ olefins.

In still another embodiment of the invention, the conditions employed are effective to form carbonaceous deposits on the catalyst.

In still another embodiment, the catalyst is heated to at least 316° C. (600° F.) in the regeneration zone prior to the step of feeding the heating fuel.

In yet another embodiment of the invention, the regeneration zone has a fuel inlet and an air inlet capable of providing an airflow through the regeneration zone, located upstream from the fuel inlet in relation to direction of the airflow, and the process further comprises (1) combusting a starting fuel with an air stream from said air inlet thereby imparting sufficient heat content within the regeneration zone to obtain the first temperature at or near the fuel inlet and (2) feeding the heating fuel through the fuel inlet.

In still another embodiment, the starting fuel employs a carbonaceous gas, e.g., natural gas.

In yet another embodiment of the invention, the starting fuel has an autoignition temperature of greater than about 482° C. (900° F.).

In another embodiment, the process of the invention further comprises filling the regeneration zone with the catalyst to a level sufficient to cover said fuel inlet before the combusting step (1), and adding additional catalyst after step (2) of feeding the heating fuel, to provide additional heated catalyst.

In still another embodiment, the catalyst is heated to at least 316° C. (600° F.) in the regeneration zone prior to the feeding step (2). heated to at least 316° C. (600° F.)

In another embodiment, the heating fuel is a liquid fuel.

In still another embodiment, at least 50 wt % of the heating fuel is a $C_{11}$–$C_{20}$ hydrocarbon fraction.

In another embodiment, at least 75 wt % of the heating fuel is a $C_{11}$–$C_{20}$ hydrocarbon fraction.

In still another embodiment, at least 85 wt % of said heating fuel is a $C_{11}$–$C_{20}$ hydrocarbon fraction.

In another embodiment, at least 75 wt % of the heating fuel is a $C_{12}$–$C_{19}$ hydrocarbon fraction and further said heating fuel has an autoignition temperature ranging from 232°–271° C. (450°–520° F.) and contains less than 10 wppm sulfur and less than 10 wppm nitrogen.

In yet another embodiment, at least 75 wt % of the heating fuel is a $C_{12}$ to $C_{16}$ hydrocarbon fraction.

In another embodiment, at least 75 wt % of the heating fuel is a $C_{12}$ to $C_{14}$ hydrocarbon fraction.

In still another embodiment, the reaction zone is cooled by steam injection.

In another embodiment, the reaction zone comprises a riser.

In yet another embodiment, the reaction zone comprises plural risers.

In still yet another embodiment, the reaction zone has two risers.

In yet another embodiment, the catalyst comprises molecular sieve having a pore diameter of less than 5.0 Angstroms.

In still yet another embodiment, the catalyst comprises at least one molecular sieve framework-type selected from the group consisting of AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, ZSM-5, ZSM-4, SAPO-34, SAPO-17, SAPO-18, MeAPSO and substituted groups thereof.

In yet another embodiment, the catalyst comprises a molecular sieve having a pore diameter of 5–10 Angstroms.

In still yet another embodiment, the catalyst comprises at least one molecular sieve framework-type selected from the group consisting of MFI, MEL, MTW, EUO, MTT, HEU, FER, AFO, AEL, TON, and substituted groups thereof.

In another embodiment, the heating step (b) occurs before the contacting step (e).

In still another embodiment, the heating step (b) occurs concurrent with the contacting step (e).

In yet another embodiment, first contacting step (a) occurs before the heating step (b).

In still another embodiment, the heating fuel contains less than 10 wppm, e.g., less than 5 wppm, sulpher and less than 10 wppm, e.g., less than 5 wppm, nitrogen.

In yet another embodiment, the invention relates to a method of adding heat to a reactor system having an oxygenate to olefin reaction zone and a catalyst regeneration zone wherein catalyst is cycled from the reaction zone to the regeneration zone and from the regeneration zone to the reaction zone, the method comprising:
  fluidizing catalyst in the regeneration zone in the presence of an oxygen containing gas;
  heating the catalyst in the regeneration zone to a first temperature;

introducing a heating fuel into the regeneration zone wherein the heating fuel has about 100 wppm or less of sulfur and has about 100 wppm or less nitrogen and an autoignition temperature greater than the first temperature but no greater than about 482° C. (900° F.) to provide a heated catalyst; and provide the heated catalyst into the reaction zone.

In yet another embodiment of the invention described immediately above, the process further comprises: contacting the catalyst with an oxygenate feedstock under conditions sufficient to convert said oxygenate to an olefin-rich product.

In still another embodiment of the invention described immediately above, the invention further comprises the process wherein said heating fuel contains a total of no greater than 20 wppm of metal selected from the group consisting of nickel and vanadium.

In yet another embodiment, the invention relates to a process for initially increasing the temperature of a reactor system for making an olefin product from an oxygenate feedstock in the presence of an oxygenate to olefin molecular sieve catalyst which process comprises:

a) contacting at least a portion of the catalyst with a regeneration medium in a regeneration zone;

b) heating said regeneration zone to a first temperature of at least 225° C. (437° F.), c) feeding to said regeneration zone a heating fuel having an autoignition temperature less than the first temperature and containing less than 100 wppm sulfur and less than 100 wppm nitrogen, thereby causing the heating fuel to ignite and provide a heated catalyst; and d) circulating said heated catalyst to the reaction zone.

In still another embodiment of the invention described immediately above, the invention comprises the process which further comprises:

e) additionally contacting the feedstock in a reaction zone with said oxygenate to olefin molecular sieve catalyst including said heated catalyst, under conditions effective to convert the feedstock into an olefin product stream.

These and other advantages of the present invention shall become apparent from the following detailed description, the attached FIGURE and the appended claims.

BRIEF DESCRIPTION OF THE DRAWING

The FIGURE provides a diagram of a reactor apparatus comprising a high velocity fluid bed with catalyst recirculation, and a regenerator having an inlet for introducing a heating fuel for initial heat-up of the reactor.

DETAILED DESCRIPTION OF THE INVENTION

As noted above, the conversion of oxygenate feedstock to olefins is an exothermic reaction. Once initiated, the reaction can sustain itself without the addition of external heat. However, there are certain circumstances in which is it necessary to add heat to the reactor/regenerator system above that generated by the conversion of oxygenate feedstock to olefins reaction. Examples include initial dry-out of the refractory linings of the reactor and regenerator system, initial preheating of the reactor prior to introduction of the oxygenate feedstock, and maintaining reaction temperature during short-term outages of the oxygenate feedstock.

The process of the present invention accomplishes this by adding supplemental heat to the regenerator by the addition of a heating fuel directly into the fluidized bed of catalyst. The fluidizing air provides the oxygen for the combustion of the heating fuel. The fluidized catalyst particles are well mixed and have sufficient heat capacity to evenly distribute the heat generated from the combustion of the heating fuel throughout the fluidized bed in the regenerator, resulting in a relatively uniform temperature within the regenerator bed. In one embodiment, this hot catalyst can be circulated to the reactor, where heat from the catalyst is transferred to the reactor. The catalyst cools as it flows through the reactor, and is then returned to the regenerator where it is re-heated. This method of adding heat can be used to dry refractory in the reactor, to preheat the reactor prior to addition of the oxygenate feedstock, and/or to maintain reaction temperature during outages of the oxygenate feedstock.

The heating fuel must have certain critical properties to be useful in the process of converting oxygenates to olefins. The autoignition temperature must be relatively low, no greater than about 454° C. (850° F.), in order to facilitate ignition of the heating fuel, and to ensure that the combustion will not be extinguished in the event of a low temperature excursion. Also, it must have low sulfur and nitrogen content, to prevent the introduction of these contaminants to the catalyst or product recovery train. The heating fuel can contain metal impurities (for example, nickel and/or vanadium) in amounts no greater than 100 wppm total metals, preferably no greater than 20 wppm total metals. In a preferred embodiment, the heating fuel can be a normally liquid fuel, e.g., a hydrocarbonaceous liquid fuel.

When converting oxygenates to a light olefin product in a reactor apparatus comprising a fluidized bed of catalyst and a regenerator for the catalyst, it is desirable to initiate operation of the apparatus by heating the reactor and catalyst to an operating temperature prior to addition of oxygenate feedstock. The process of the present invention accomplishes this, in one embodiment, by heating the regeneration zone by combusting a starting fuel, preferably a gaseous carbonaceous fuel, such as light gas or natural gas, with an air stream at or upstream of the regenerator air inlet. A portion of the oxygenate conversion catalyst is added to the regeneration zone to a level sufficient to cover the fuel inlet of the regenerator. In one embodiment, the catalyst in the regeneration zone is heated to a temperature of at least 225° C. This imparts sufficient heat content within the regeneration zone to initiate and sustain ignition of a heating fuel that is then introduced at a rate sufficient to achieve a temperature sufficient to convert oxygenate to olefins upon contact with the catalyst. In one embodiment, the heating fuel is a normally liquid fuel comprising a $C_{11}$–$C_{20}$ hydrocarbon fraction having an autoignition temperature less than 482° C. (900° F.) and containing less than 200 wppm sulfur and less than 500 wppm nitrogen as elemental species, i.e. (S or N). The heating fuel is fed through the regenerator fuel inlet to the heated regeneration zone and ignites under appropriate temperature conditions in the regenerator, resulting in heating of the catalyst. Additional catalyst can be added along with the heating fuel as needed, to the heated regeneration zone. The resulting heated catalyst is circulated to the reaction zone. In one embodiment the circulation of the catalyst heats the reaction zone to a reaction zone temperature of at least 316° C. (600° F.) which is sufficient to effect catalytic conversion of oxygenates to olefins. Optionally, the catalyst in the reaction zone is circulated back to the regeneration zone.

In the process of one embodiment, a feed, including an oxygenate and any diluents, is contacted in a reactor, or a reaction zone, with a catalyst at effective process conditions so as to produce a product including light olefins. These process conditions include an effective temperature, pressure, WHSV (weight hourly space velocity), gas superficial velocity and, optionally, an effective amount of diluent, correlated to produce light olefins. These process conditions are described below in detail.

Desirably, the rate of catalyst, comprising molecular sieve and any other materials such as binders, fillers, etc., recirculated to contact the feed is from about 1 to about 100 times, more desirably from about 10 to about 80 times, and most desirably from about 10 to about 50 times the total feed rate of oxygenates to the reactor. Desirably, a portion of the catalyst, comprising molecular sieve and any other materials such as binders, fillers, etc., is removed from the reactor for regeneration and recirculation back to the reactor at a rate of from about 0.1 times to about 10 times, more desirably from about 0.2 to about 5 times, and most desirably from about 0.3 to about 3 times the total feed rate of oxygenates to the reactor.

The temperature useful to convert oxygenates to light olefins varies over a wide range depending, at least in part, on the catalyst, the fraction of regenerated catalyst in a catalyst mixture, and the configuration of the reactor apparatus and the reactor. Although the present invention is not limited to a particular temperature, best results are obtained if the process is conducted at a temperature from about 316° C. to about 700° C., desirably from about 316° C. to about 600° C., and most desirably from about 316° C. to about 500° C. Lower temperatures generally result in lower rates of reaction, and the formation rate of the desired light olefin products typically become markedly slower. However, at temperatures greater than 700° C., there is the possibility that the process will not form an optimum amount of light olefin products, and the rate at which coke and light saturates form on the catalyst becomes too high.

Light olefins will form—although not necessarily in optimum amounts—at a wide range of pressures including, but not limited to, autogeneous pressures and pressures from about 0.1 kPa to about 100 MPa. A desired pressure is from about 6.9 kPa to about 34 MPa and most desirably from about 20 kPa to about 500 kPa. The foregoing pressures do not include that of a diluent, if any, and refer to the partial pressure of the feed as it relates to oxygenate compounds and/or mixtures thereof. Typically, pressures outside of the stated ranges are used and are not excluded from the scope of the invention. In some circumstances, lower and upper extremes of pressure adversely affect selectivity, conversion, coking rate, and/or reaction rate; however, light olefins will still form and, for that reason, these extremes of pressure are considered part of the present invention.

The process of the present invention is continued for a period of time sufficient to produce the desired light olefins. A steady state or semi-steady state production of light olefins is attainable during this period of time, largely determined by the reaction temperature, the pressure, the catalyst selected, the amount of recirculated spent catalyst, the level of regeneration, the weight hourly space velocity, the superficial velocity, and other selected process design characteristics.

A wide range of WHSV's for the oxygenate conversion reaction, defined as weight of total oxygenate to the reaction zone per hour per weight of molecular sieve in the catalyst in the reaction zone, function with the present invention. The total oxygenate to the reaction zone includes all oxygenate in both the vapor and liquid phase. Although the catalyst often contains other materials which act as inerts, fillers or binders, the WHSV is calculated using only the weight of molecular sieve in the catalyst in the reaction zone. The WHSV is desirably high enough to maintain the catalyst in a fluidized state under the reaction conditions and within the reactor configuration and design. Generally, the WHSV is from about 1 $hr^{-1}$ to about 5000 $hr^{-1}$, desirably from about 2 $hr^{-1}$ to about 3000 $hr^{-1}$, and most desirably from about 5 $hr^{-1}$ to about 1500 $hr^{-1}$. For a feed comprising methanol, dimethyl ether, or mixtures thereof, the WHSV is desirably at least about 20 $hr^{-1}$ and more desirably from about 20 $hr^{-1}$ to about 300 $hr^{-1}$.

Oxygenate conversion should be maintained sufficiently high to avoid the need for commercially unacceptable levels of feed recycling. While 100% oxygenate conversion is desired for the purpose of completely avoiding feed recycle, a reduction in unwanted by-products is observed frequently when the conversion is about 98% or less. Since recycling up to as much as about 50% of the feed can be commercially acceptable, conversion rates from about 50% to about 98% are desired. According to one embodiment, conversion rates are maintained in this range—50% to about 98%—using a number of methods familiar to persons of ordinary skill in the art. Examples include, but are not necessarily limited to, adjusting one or more of the following: reaction temperature; pressure; flow rate (weight hourly space velocity and/or gas superficial velocity); catalyst recirculation rate; reactor apparatus configuration; reactor configuration; feed composition; amount of liquid feed relative to vapor feed; amount of recirculated catalyst; degree of catalyst regeneration; and other parameters which affect the conversion.

During the conversion of oxygenates to light olefins, carbonaceous deposits accumulate on the catalyst used to promote the conversion reaction. At some point, the build up of these carbonaceous deposits causes a reduction in the capability of the catalyst to convert the oxygenate feed to light olefins. At this point, the catalyst is partially deactivated. When a catalyst can no longer convert an oxygenate to an olefin product, the catalyst is considered to be fully deactivated. As a step in the process of the present invention, a portion of the catalyst is withdrawn from the reactor apparatus and at least a portion of the portion removed from the reactor is partially, if not fully, regenerated in a regenerator. By regeneration, it is meant that the carbonaceous deposits are at least partially removed from the catalyst. Desirably, the portion of the catalyst withdrawn from the reactor is at least partially deactivated. The remaining portion of the catalyst in the reactor apparatus is recirculated without regeneration. The regenerated catalyst, with or without cooling, is then returned to the reactor. Desirably, the rate of withdrawing the portion of the catalyst for regeneration is from about 0.1% to about 99% of the rate of the catalyst exiting the reactor. More desirably, the rate is from about 0.2% to about 50%, and, most desirably, from about 0.5% to about 5%.

According to an embodiment, the catalyst is regenerated in any number of methods—batch, continuous, semi-continuous, or a combination thereof. Continuous catalyst regeneration is a desired method. Desirably, the catalyst is regenerated to a level of remaining coke from about 0.01 wt % to about 15 wt % of the weight of the catalyst.

The catalyst regeneration temperature should be from about 250° C. to about 750° C., and desirably from about 500° C. to about 725° C. The temperature in the regenerator can be controlled by removing excess heat. Desirably, catalyst regeneration is carried out at least partially deactivated catalyst that has been stripped of most of readily removable organic materials (organics) in a stripper or stripping chamber first. This stripping can be achieved by passing a stripping gas over the spent catalyst at an elevated temperature. Gases suitable for stripping include steam, nitrogen, helium, argon, methane, $CO_2$, CO, hydrogen, and mixtures thereof. A preferred gas is steam. Gas hourly space velocity (GHSV, based on volume of gas to volume of catalyst and coke) of the stripping gas is from about 0.1 $h^{-1}$ to about 20,000 $h^{-1}$. Acceptable temperatures of stripping are from about 250° C. to about 750° C., and desirably from about 350° C. to about 675° C.

The process of the present invention for converting oxygenates to light olefins employs a feed including an oxygenate. As used herein, the term "oxygenate" is defined to include, but is not necessarily limited to, hydrocarbons containing oxygen such as the following: aliphatic alcohols, ethers, carbonyl compounds (aldehydes, ketones, carboxylic acids, carbonates, and the like), and mixtures thereof. The aliphatic moiety desirably should contain in the range of from about 1–10 carbon atoms and more desirably in the range of from about 1–4 carbon atoms. Representative oxygenates include, but are not necessarily limited to, lower straight chain or branched aliphatic alcohols, and their unsaturated counterparts. Examples of suitable oxygenates include, but are not necessarily limited to the following: methanol; ethanol; n-propanol; isopropanol; $C_4$–$C_{10}$ alcohols; methyl ethyl ether; dimethyl ether; diethyl ether; di-isopropyl ether; methyl formate; formaldehyde; di-methyl carbonate; methyl ethyl carbonate; acetone; and mixtures thereof. Desirably, the oxygenate used in the conversion reaction is selected from the group consisting of methanol, dimethyl ether and mixtures thereof. More desirably the oxygenate is methanol. The total charge of feed to the reactor apparatus can contain additional components, such as diluents.

One or more diluents can be fed to the reaction zone with the oxygenates, such that the total feed mixture comprises diluent in a range of from about 1 mol % and about 99 mol %. Diluents which can be employed in the process include, but are not necessarily limited to, helium, argon, nitrogen, carbon monoxide, carbon dioxide, hydrogen, water, paraffins, other hydrocarbons (such as methane), aromatic compounds, and mixtures thereof. Desired diluents include, but are not necessarily limited to, water and nitrogen.

The catalyst suitable for catalyzing the oxygenate-to-olefin conversion reaction of the present invention includes a molecular sieve and mixtures of molecular sieves. Molecular sieves can be zeolitic (zeolites) or non-zeolitic (non-zeolites). Useful catalysts can also be formed from mixtures of zeolitic and non-zeolitic molecular sieves. Desirably, the catalyst includes a non-zeolitic molecular sieve. Desired molecular sieves for use with the process of the present invention include "small" and "medium" pore molecular sieves. "Small pore" molecular sieves are defined as molecular sieves with pores having a diameter of less than about 5.0 Angstroms. "Medium pore" molecular sieves are defined as molecular sieves with pores having a diameter from about 5.0 to about 10.0 Angstroms.

Molecular sieves are porous solids having pores of different sizes such as zeolites or zeolite-type molecular sieves, carbons and oxides. There are amorphous and crystalline molecular sieves. Molecular sieves include natural, mineral molecular sieves, or chemically formed, synthetic molecular sieves that are typically crystalline materials containing silica, and optionally alumina. The most commercially useful molecular sieves for the petroleum and petrochemical industries are known as zeolites. A zeolite is an aluminosilicate having an open framework structure that usually carries negative charges. This negative charge within portions of the framework is a result of an $Al^{3+}$ replacing a $Si^{4+}$. Cations counter-balance these negative charges preserving the electroneutrality of the framework, and these cations are exchangeable with other cations and/or protons. Synthetic molecular sieves, particularly zeolites, are typically synthesized by mixing sources of alumina and silica in a strongly basic aqueous media, often in the presence of a structure directing agent or templating agent. The structure of the molecular sieve formed is determined in part by solubility of the various sources, silica-to-alumina ratio, nature of the cation, synthesis temperature, order of addition, type of templating agent, and the like.

A zeolite is typically formed from corner sharing the oxygen atoms of $[SiO_4]$ and $[AlO_4]$ tetrahedra or octahedra. Zeolites in general have a one-, two- or three-dimensional crystalline pore structure having uniformly sized pores of molecular dimensions that selectively adsorb molecules that can enter the pores, and exclude those molecules that are too large. The pore size, pore shape, interstitial spacing or channels, composition, crystal morphology and structure are a few characteristics of molecular sieves that determine their use in various hydrocarbon adsorption and conversion processes.

There are many different types of zeolites well known to convert a feedstock, especially oxygenate containing feedstock, into one or more olefin(s). For example, U.S. Pat. No. 5,367,100 describes the use of a well known zeolite, ZSM-5, to convert methanol into olefin(s); U.S. Pat. No. 4,062,905 discusses the conversion of methanol and other oxygenates to ethylene and propylene using crystalline aluminosilicate zeolites, for example Zeolite T, ZK5, erionite and chabazite; and U.S. Pat. No. 4,079,095 describes the use of ZSM-34 to convert methanol to hydrocarbon products such as ethylene and propylene.

Crystalline aluminophosphates, $ALPO_4$, formed from corner sharing $[AlO_2]$ and $[PO_2]$ tetrahedra linked by shared oxygen atoms are described in U.S. Pat. No. 4,310,440 to produce light olefin(s) from an alcohol. Metal containing aluminophosphate molecular sieves, MeAPO's and ElAPO's, have been also described to convert alcohols into olefin(s). MeAPO's have a $[MeO_2]$, $[AlO_2]$ and $[PO_2]$ tetrahedra microporous structure, where Me is a metal source having one or more of the divalent elements Co, Fe, Mg, Mn and Zn, and trivalent Fe from the Periodic Table of Elements. ElAPO's have an $[ElO_2]$, $[AlO_2]$ and $[PO_2]$ tetrahedra microporous structure, where El is a metal source having one or more of the elements As, B, Be, Ga, Ge, Li, Ti and Zr. MeAPO's and ElAPO's are typically synthesized by the hydrothermal crystallization of a reaction mixture of a metal source, an aluminum source, a phosphorous source and a templating agent. The preparation of MeAPO's and ElAPO's are found in U.S. Pat. Nos. 4,310,440, 4,500,651, 4,554,143, 4,567,029, 4,752,651, 4,853,197, 4,873,390 and 5,191,141.

One of the most useful molecular sieves for converting methanol to olefin(s) are those ELAPO's or MeAPO's where the metal source is silicon, often a fumed, colloidal or precipitated silica. These molecular sieves are known as silicoaluminophosphate molecular sieves. Silicoaluminophosphate (SAPO) molecular sieves contain a three-dimensional microporous crystalline framework structure of $[SiO_2]$, $[AlO_2]$ and $[PO_2]$ corner sharing tetrahedral units. SAPO synthesis is described in U.S. Pat. No. 4,440,871, which is herein fully incorporated by reference. SAPO is generally synthesized by the hydrothermal crystallization of a reaction mixture of silicon-, aluminum- and phosphorus-sources and at least one templating agent. Synthesis of a SAPO molecular sieve, its formulation into a SAPO catalyst, and its use in converting a hydrocarbon feedstock into olefin(s), particularly where the feedstock is methanol, are shown in U.S. Pat. Nos. 4,499,327, 4,677,242, 4,677,243, 4,873,390, 5,095,163, 5,714,662 and 6,166,282, all of which are herein fully incorporated by reference.

Molecular sieves have various chemical and physical, framework, characteristics. Molecular sieves have been well classified by the Structure Commission of the International Zeolite Association according to the rules of the IUPAC Commission on Zeolite Nomenclature. A framework-type describes the connectivity, topology, of the tetrahedrally coordinated atoms constituting the framework, and making an abstraction of the specific properties for those materials. Framework-type zeolite and zeolite-type molecular sieves for which a structure has been established, are assigned a three letter code and are described in the *Atlas of Zeolite Framework Types*, 5th edition, Elsevier, London, England (2001), which is herein fully incorporated by reference.

Non-limiting examples of these molecular sieves are the small pore molecular sieves of framework-type selected from the group consisting of AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof; the medium pore molecular sieves of framework-type selected from the group consisting of AFO, AEL, EUO, HEU, FER, MEL, MFI, MTW, MTT, TON, and substituted forms thereof; and the large pore molecular sieves of framework-type selected from the group consisting of EMT, FAU, and substituted forms thereof. Other molecular sieves include framework-types selected from the group consisting of ANA, BEA, CFI, CLO, DON, GIS, LTL, MER, MOR, MWW and SOD. Non-limiting examples of a preferred molecular sieve framework-types, particularly for converting an oxygenate containing feedstock into olefin(s), are selected from the group consisting of AEL, AFY, BEA, CHA, EDI, FAU, FER, GIS, LTA, LTL, MER, MFI, MOR, MTT, MWW, TAM and TON. In one preferred embodiment, the molecular sieve of the invention has an AEI topology or a CHA topology, or a combination thereof, most preferably a CHA topology.

Molecular sieve materials all have 3-dimensional, four-connected framework structure of corner-sharing $TO_4$ tetrahedra, where T is any tetrahedrally coordinated cation. These molecular sieves are typically described in terms of the size of the ring that defines a pore, where the size is based on the number of T atoms in the ring. Other framework-type characteristics include the arrangement of rings that form a cage, and when present, the dimension of channels, and the spaces between the cages. See van Bekkum, et al., *Introduction to Zeolite Science and Practice, Second Completely Revised and Expanded Edition*, Volume 137, pages 1–67, Elsevier Science, B.V., Amsterdam, Netherlands (2001).

The small, medium and large pore molecular sieves have from a 4-ring to a 12-ring or greater framework-type. In a preferred embodiment, the zeolitic molecular sieves have 8-, 10- or 12-ring structures or larger and an average pore size in the range of from about 3 Å to 15 Å. In the most preferred embodiment, the molecular sieves of the invention, preferably silicoaluminophosphate molecular sieves have 8-rings and an average pore size less than about 5 Å, preferably in the range of from 3 Å to about 5 Å, more preferably from 3 Å to about 4.5 Å, and most preferably from 3.5 Å to about 4.2 Å.

Molecular sieves, particularly zeolitic and zeolitic-type molecular sieves, preferably have a molecular framework of one, preferably two or more corner-sharing $[TO_4]$ tetrahedral units, more preferably, two or more $[SiO_4]$, $[AlO_4]$ and/or $[PO_4]$ tetrahedral units, and most preferably $[SiO_4]$, $[AlO_4]$ and $[PO_4]$ tetrahedral units. These silicon, aluminum, and phosphorous based molecular sieves and metal containing silicon, aluminum and phosphorous based molecular sieves have been described in detail in numerous publications including for example, U.S. Pat. No. 4,567,029 (MeAPO where Me is Mg, Mn, Zn, or Co), U.S. Pat. No. 4,440,871 (SAPO), European Patent Application EP-A-0 159 624 (ELAPSO where El is As, Be, B, Cr, Co, Ga, Ge, Fe, Li, Mg, Mn, Ti or Zn), U.S. Pat. No. 4,554,143 (FeAPO), U.S. Pat. Nos. 4,822,478, 4,683,217, 4,744,885 (FeAPSO), EP-A-0 158 975 and U.S. Pat. No. 4,935,216 (ZnAPSO, EP-A-0 161 489 (CoAPSO), EP-A-0 158 976 (ELAPO, where EL is Co, Fe, Mg, Mn, Ti or Zn), U.S. Pat. No. 4,310,440 ($AlPO_4$), EP-A-0 158 350 (SENAPSO), U.S. Pat. No. 4,973,460 (LiAPSO), U.S. Pat. No. 4,789,535 (LiAPO), U.S. Pat. No. 4,992,250 (GeAPSO), U.S. Pat. No. 4,888,167 (GeAPO), U.S. Pat. No. 5,057,295 (BAPSO), U.S. Pat. No. 4,738,837 (CrAPSO), U.S. Pat. Nos. 4,759,919, and 4,851,106 (CrAPO), U.S. Pat. Nos. 4,758,419, 4,882,038, 5,434,326 and 5,478,787 (MgAPSO), U.S. Pat. No. 4,554,143 (FeAPO), U.S. Pat. No. 4,894,213 (AsAPSO), U.S. Pat. No. 4,913,888 (AsAPO), U.S. Pat. Nos. 4,686,092, 4,846,956 and 4,793,833 (MnAPSO), U.S. Pat. Nos. 5,345,011 and 6,156,931 (MnAPO), U.S. Pat. No. 4,737,353 (BeAPSO), U.S. Pat. No. 4,940,570 (BeAPO), U.S. Pat. Nos. 4,801,309, 4,684,617 and 4,880,520 (TiAPSO), U.S. Pat. Nos. 4,500,651, 4,551,236 and 4,605,492 (TiAPO), U.S. Pat. Nos. 4,824,554, 4,744,970 (CoAPSO), U.S. Pat. No. 4,735,806 (GaAPSO) EP-A-0 293 937 (QAPSO, where Q is framework oxide unit $[QO_2]$), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,241,093, 5,493,066 and 5,675,050, all of which are herein fully incorporated by reference.

Other molecular sieves include those described in EP-0 888 187 B1 (microporous crystalline metallophosphates, $SAPO_4$ (UIO-6)), U.S. Pat. No. 6,004,898 (molecular sieve and an alkaline earth metal), U.S. patent application Ser. No. 09/511,943 filed Feb. 24, 2000 (integrated hydrocarbon co-catalyst), PCT WO 01/64340 published Sep. 7, 2001 (thorium containing molecular sieve), and R. Szostak, *Handbook of Molecular Sieves*, Van Nostrand Reinhold, New York, N.Y. (1992), which are all herein fully incorporated by reference.

The more preferred silicon, aluminum and/or phosphorous containing molecular sieves, and aluminum, phosphorous, and optionally silicon, containing molecular sieves include aluminophosphate (ALPO) molecular sieves and silicoaluminophosphate (SAPO) molecular sieves and substituted, preferably metal substituted, ALPO and SAPO molecular sieves. The most preferred molecular sieves are SAPO molecular sieves, and metal substituted SAPO molecular sieves. In an embodiment, the metal is an alkali metal of Group IA of the Periodic Table of Elements, an alkaline earth metal of Group IIA of the Periodic Table of Elements, a rare earth metal of Group IIIB, including the Lanthanides: lanthanum, cerium, praseodymium, neodymium, samarium, europium, gadolinium, terbium, dysprosium, holmium, erbium, thulium, ytterbium and lutetium; and scandium or yttrium of the Periodic Table of Elements, a transition metal of Groups IVB, VB, VIB, VIIB, VIIIB, and IB of the Periodic Table of Elements, or mixtures of any of these metal species. In one preferred embodiment, the metal is selected from the group consisting of Co, Cr, Cu, Fe, Ga, Ge, Mg, Mn, Ni, Sn, Ti, Zn and Zr, and mixtures thereof. In another preferred embodiment, these metal atoms discussed above are inserted into the framework of a molecular sieve through a tetrahedral unit, such as [MeO$_2$], and carry a net charge depending on the valence state of the metal substituent. For example, in one embodiment, when the metal substituent has a valence state of +2, +3, +4, +5, or +6, the net charge of the tetrahedral unit is between −2 and +2.

In one embodiment, the molecular sieve, as described in many of the U.S. patents mentioned above, is represented by the empirical formula, on an anhydrous basis:

$$mR:(M_xAl_yP_z)O_2$$

wherein R represents at least one templating agent, preferably an organic templating agent; m is the number of moles of R per mole of $(M_xAl_yP_z)O_2$ and m has a value from 0 to 1, preferably 0 to 0.5, and most preferably from 0 to 0.3; x, y, and z represent the mole fraction of Al, P and M as tetrahedral oxides, where M is a metal selected from one of Group IA, IIA, IB, IIIB, IVB, VB, VIB, VIIB, VIIIB and Lanthanide's of the Periodic Table of Elements, preferably M is selected from one of the group consisting of Co, Cr, Cu, Fe, Ga, Ge, Mg, Mn, Ni, Sn, Ti, Zn and Zr. In an embodiment, m is greater than or equal to 0.2, and x, y and z are greater than or equal to 0.01.

In another embodiment, m is greater than 0.1 to about 1, x is greater than 0 to about 0.25, y is in the range of from 0.4 to 0.5, and z is in the range of from 0.25 to 0.5, more preferably m is from 0.15 to 0.7, x is from 0.01 to 0.2, y is from 0.4 to 0.5, and z is from 0.3 to 0.5.

Non-limiting examples of SAPO and ALPO molecular sieves of the invention include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44 (U.S. Pat. No. 6,162,415), SAPO-47, SAPO-56, ALPO-5, ALPO-11, ALPO-18, ALPO-31, ALPO-34, ALPO-36, ALPO-37, ALPO-46, and metal containing molecular sieves thereof. The more preferred zeolite-type molecular sieves include one or a combination of SAPO-18, SAPO-34, SAPO-35, SAPO-44, SAPO-56, ALPO-18 and ALPO-34, even more preferably one or a combination of SAPO-18, SAPO-34, ALPO-34 and ALPO-18, and metal containing molecular sieves thereof, and most preferably one or a combination of SAPO-34 and ALPO-18, and metal containing molecular sieves thereof.

In an embodiment, the molecular sieve is an intergrowth material having two or more distinct phases of crystalline structures within one molecular sieve composition. In particular, intergrowth molecular sieves are described in the combination of U.S. patent application Ser. No. 09/924,016 filed Aug. 7, 2001 and PCT WO 98/15496 published Apr. 16, 1998, both of which are herein fully incorporated by reference. In another embodiment, the molecular sieve comprises at least one intergrown phase of AEI and CHA framework-types. For example, SAPO-18, ALPO-18 and RUW-18 have an AEI framework-type, and SAPO-34 has a CHA framework-type.

The synthesis of molecular sieves is described in many of the references discussed above. Generally, molecular sieves are synthesized by the hydrothermal crystallization of one or more of a source of aluminum, a source of phosphorous, a source of silicon, a templating agent, and a metal containing compound. Typically, a combination of sources of silicon, aluminum and phosphorous, optionally with one or more templating agents and/or one or more metal containing compounds are placed in a sealed pressure vessel, optionally lined with an inert plastic such as polytetrafluoroethylene, and heated, under a crystallization pressure and temperature, until a crystalline material is formed, and then recovered by filtration, centrifugation and/or decanting.

In a preferred embodiment the molecular sieves are synthesized by forming a reaction product of a source of silicon, a source of aluminum, a source of phosphorous, an organic templating agent, preferably a nitrogen containing organic templating agent, and one or more polymeric bases. This particularly preferred embodiment results in the synthesis of a silicoaluminophosphate crystalline material that is then isolated by filtration, centrifugation and/or decanting.

Non-limiting examples of silicon sources include silicates, fumed silica, for example, Aerosil-200 available from Degussa Inc., New York, N.Y., and CAB-O-SIL M-5, silicon compounds such as tetraalkyl orthosilicates, for example, tetramethyl orthosilicate (TMOS) and tetraethylsilicate (TEOS), colloidal silicas or aqueous suspensions thereof, for example Ludox-HS-40 sol available from E. I. du Pont de Nemours, Wilmington, Del., silicic acid, alkali-metal silicate, or any combination thereof. The preferred source of silicon is a silica sol.

Non-limiting examples of aluminum sources include aluminum-containing compositions such as aluminum alkoxides, for example aluminum isopropoxide, aluminum phosphate, aluminum hydroxide, sodium aluminate, pseudo-boehmite, gibbsite and aluminum trichloride, or any combinations thereof. A preferred source of aluminum is pseudo-boehmite, particularly when producing a silicoaluminophosphate molecular sieve.

Non-limiting examples of phosphorus sources, which can also include aluminum-containing phosphorous compositions, include phosphorus-containing, inorganic or organic, compositions such as phosphoric acid, organic phosphates such as triethyl phosphate, and crystalline or amorphous aluminophosphates such as ALPO$_4$, phosphorus salts, or combinations thereof. The preferred source of phosphorus is phosphoric acid, particularly when producing a silicoaluminophosphate.

Templating agents are generally compounds that contain elements of Group VA of the Periodic Table of Elements, particularly nitrogen, phosphorus, arsenic and antimony, more preferably nitrogen or phosphorous, and most preferably nitrogen. Typical templating agents of Group VA of the Periodic Table of elements also contain at least one alkyl or aryl group, preferably an alkyl or aryl group having from 1 to 10 carbon atoms, and more preferably from 1 to 8 carbon atoms. The preferred templating agents are nitrogen-containing compounds such as amines and quaternary ammonium compounds.

The quaternary ammonium compounds, in one embodiment, are represented by the general formula $R_4N^+$, where each R is hydrogen or a hydrocarbyl or substituted hydrocarbyl group, preferably an alkyl group or an aryl group having from 1 to 10 carbon atoms. In one embodiment, the templating agents include a combination of one or more quaternary ammonium compound(s) and one or more of a mono-, di- or tri-amine.

Non-limiting examples of templating agents include tetraalkyl ammonium compounds including salts thereof such as tetramethyl ammonium compounds including salts thereof, tetraethyl ammonium compounds including salts thereof, tetrapropyl ammonium including salts thereof, and tetrabutylammonium including salts thereof, cyclohexylamine, morpholine, di-n-propylamine (DPA), tripropylamine, triethylamine (TEA), triethanolamine, piperidine, cyclohexylamine, 2-methylpyridine, N,N-dimethylbenzylamine, N,N-diethylethanolamine, dicyclohexylamine, N,N-dimethylethanolamine, choline, N,N'-dimethylpiperazine, 1,4-diazabicyclo(2,2,2)octane, N',N',N,N-tetramethyl-(1,6)hexanediamine, N-methyldiethanolamine, N-methyl-ethanolamine, N-methyl piperidine, 3-methyl-piperidine, N-methylcyclohexylamine, 3-methylpyridine, 4-methylpyridine, quinuclidine, N,N'-dimethyl-1,4-diazabicyclo(2,2,2) octane ion; di-n-butylamine, neopentylamine, di-n-pentylamine, isopropylamine, t-butyl-amine, ethylenediamine, pyrrolidine, and 2-imidazolidone.

The preferred templating agent or template is a tetraethylammonium compound, such as tetraethyl ammonium hydroxide (TEAOH), tetraethyl ammonium phosphate, tetraethyl ammonium fluoride, tetraethyl ammonium bromide, tetraethyl ammonium chloride and tetraethyl ammonium acetate. The most preferred templating agent is tetraethyl ammonium hydroxide and salts thereof, particularly when producing a silicoaluminophosphate molecular sieve. In one embodiment, a combination of two or more of any of the above templating agents is used in combination with one or more of a silicon-, aluminum-, and phosphorous-source, and a polymeric base.

The molecular sieve can also be incorporated into a solid composition, preferably solid particles, in which the molecular sieve is present in an amount effective to catalyze the desired conversion reaction. The solid particles can include a catalytically effective amount of the molecular sieve and matrix material, preferably at least one of a filler material and a binder material, to provide a desired property or properties, e.g., desired catalyst dilution, mechanical strength and the like, to the solid composition. Such matrix materials are often to some extent porous in nature and often have some nonselective catalytic activity to promote the formation of undesired products and may or may not be effective to promote the desired chemical conversion. Such matrix, e.g., filler and binder, materials include, for example, synthetic and naturally occurring substances, metal oxides, clays, silicas, aluminas, silica-aluminas, silica-magnesias, silica-zirconias, sili-cathorias, silica-beryllias, silica-titanias, silica-alumina-thorias, silica-aluminazirconias, and mixtures of these materials.

The solid catalyst composition preferably comprises about 1% to about 99%, more preferably about 5% to about 90%, and still more preferably about 10% to about 80%, by weight of molecular sieve; and an amount of about 1% to about 99%, more preferably about 5% to about 90%, and still more preferably about 10% to about 80%, by weight of matrix material.

The preparation of solid catalyst compositions, e.g., solid particles, comprising the molecular sieve and matrix material, is conventional and well known in the art and, therefore, is not discussed in detail here.

The catalyst can further contain binders, fillers, or other material to provide better catalytic performance, attrition resistance, regenerability, and other desired properties. Desirably, the catalyst is fluidizable under the reaction conditions. The catalyst should have particle sizes of from about 1$\mu$ to about 3,000$\mu$, desirably from about 5$\mu$ to about 300$\mu$, and more desirably from about 5$\mu$ to about 200$\mu$. The catalyst can be subjected to a variety of treatments to achieve the desired physical and chemical characteristics. Such treatments include, but are not necessarily limited to, calcination, ball milling, milling, grinding, spray drying, hydrothermal treatment, acid treatment, base treatment, and combinations thereof.

As additional methods for controlling the heat generated by the conversion reaction and, subsequently, the temperature differential in the reactor, the present invention can include one or more or all of the following steps: providing a portion of the oxygenate portion of the feed to the reactor in a liquid form; providing at least a portion of the diluent to the reactor in a liquid form; and providing non-reactive solids to the reactor apparatus.

When a portion of the feed is provided in a liquid form, the liquid portion of the feed can be either oxygenate, diluent or a mixture of both. The liquid portion of the feed can be directly injected into the reactor, or entrained or otherwise carried into the reactor with the vapor portion of the feed or a suitable carrier gas/diluent. By providing a portion of the feed (oxygenate and/or diluent) in the liquid phase, the temperature differential in the reactor can be further controlled. The exothermic heat of reaction of oxygenate conversion is partially absorbed by the endothermic heat of vaporization of the liquid portion of the feed. Controlling the proportion of liquid feed to vapor feed fed to the reactor thus allows control of the temperature differential in the reactor. Introduction of liquid feed to the reactor acts in concert with the recirculation of catalyst and non-reactive solids, providing another independent variable to improve overall control of the temperature in the reactor.

The amount of feed provided in a liquid form, whether fed separately or jointly with the vapor feed, is from about 0.1 wt. % to about 85 wt. % of the total oxygenate content plus diluent in the feed. More desirably, the range is from about 1 wt. % to about 75 wt. % of the total oxygenate plus diluent feed, and most desirably the range is from about 5 wt. % to about 65 wt. %. The liquid and vapor portions of the feed can be the same composition, or can contain varying proportions of the same or different oxygenates and same or different diluents. One particularly effective liquid diluent is water, due to its relatively high heat of vaporization, which allows for a high impact on the reactor temperature differential with a relatively small rate. Other useful diluents are described above. Proper selection of the temperature and pressure of any appropriate oxygenate and/or diluent being fed to the reactor will ensure at least a portion is in the liquid phase as it enters the reactor and/or comes into contact with the catalyst or a vapor portion of the feed and/or diluent.

Optionally, the liquid fraction of the feed can be split into portions and introduced to the inlet zone and at a multiplicity of locations along the length of the reactor. According to one embodiment, this is done with either the oxygenate feed, the diluent or both. Typically, this is done with the diluent portion of the feed. Another option is to provide a nozzle which introduces the total liquid fraction of the feed to the inlet zone or reactor in a manner such that the nozzle forms liquid droplets of an appropriate size distribution which, when entrained with the gas and solids introduced to the inlet zone or reactor, vaporize gradually along the length of the reactor. Either of these arrangements or a combination thereof can be used to better control the temperature differential in the reactor. The means of introducing a multiplicity of liquid feed points in a reactor or designing a liquid feed nozzle to control droplet size distribution is well known in the art and is not discussed here, except in relation to introduction of the liquid fuel to the regenerator.

Non-reactive solids which contain no molecular sieve are mixed with the catalyst solids, and used in the reactor, and recirculated to the reactor and regenerator in one embodiment. These non-reactive solids have the same capability as the catalyst to provide inertial mass to control temperature rise in the reactor, but are substantially inert for the purposes of oxygenate conversion. Suitable materials for use as non-reactive solids are metals, metal oxides, and mixtures thereof. Particularly suitable materials are those used as matrices for the catalyst formulation, e.g., fillers and binders such as silicas and aluminas, among others, and mixtures thereof. Desirably, the non-reactive solids should have a heat capacity of from about 0.05 to about 1 cal/g-° C., more preferably from about 0.1 to about 0.8 cal/g-° C., and most preferably from about 0.1 to about 0.5 cal/g-° C. Further, desirably, the mass proportion of non-reactive solids to catalyst is from about 0.01 to about 10, more desirably from about 0.05 to about 5.

One skilled in the art will appreciate that the non-reactive solids can also be regenerated with the catalyst in the manner described above.

The process of the present invention is desirably carried out in a reactor apparatus which comprises an inlet zone, a reaction zone, and a disengaging zone. In one embodiment, the superficial gas velocity in the reaction zone is above about 1 m/s and preferrably above about 2 m/s. When the process of the present invention is conducted in this type of reactor apparatus, at least a portion of the catalyst/solids is recirculated from the disengaging zone to the inlet zone to maintain the reactor at near isothermal conditions. At least a portion of the vapor feed then mixes with the catalyst/solids in the inlet zone and is directed to the reaction zone in which the oxygenate to olefin conversion reaction takes place. Optionally, a liquid feed and/or diluent portion of the total feed or various sub-portions thereof can be directed to the inlet zone and/or to one or more locations in the reaction zone. With this apparatus, the catalyst/solids can be recirculated either inside the reactor apparatus or external to the rector apparatus as the catalyst/solids are recirculated from the disengaging zone to the inlet zone and/or the reaction zone. As also described, an additional portion of the catalyst/solids can optionally be removed from the reactor apparatus and sent to a regenerator to regenerate the catalyst. Catalyst/solids from the regenerator can be returned to any of the three zones, or can be directed to a conduit which serves to recirculate the catalyst/solids from the disengaging zone to the inlet zone or reaction zone.

A preferred embodiment of a reactor system for the present invention is a circulating fluid bed reactor with continuous regeneration, similar to a modern fluid catalytic cracker. Fixed beds are not practical for the process because oxygenate to olefin conversion is a highly exothermic process which requires several stages with intercoolers or other cooling devices. The reaction also results in a high pressure drop due to the production of low pressure, low density gas.

It is important for the reactor to be designed such that a relatively high average level of coke on catalyst (or carbon atoms per catalyst active site) is maintained—an amount greater than about 1.5 wt %, preferably in the range of from about 2 wt % to about 30 wt %, most preferably in the range of from about 2 wt % to about 20 wt %. If the reactor is a high velocity fluidized bed reactor (sometimes referred to as a riser reactor), then a portion of the catalyst exiting the top of the reactor must be returned to the reactor inlet via a catalyst recirculation conduit. This is different from a typical Fluid Catalytic Cracker (FCC) riser reactor, where all or most of the catalyst exiting the top of the reactor is sent to the regenerator. The return of coked catalyst directly to the reactor, without regenerating the coked catalyst, allows the average coke level of the catalyst in the reactor to build up to a preferred level. By adjusting the ratio of the flow of the coked catalyst between the regenerator and the reactor, a preferred level of coking, or "desirable carbonaceous deposits," can be maintained.

Figure 1:
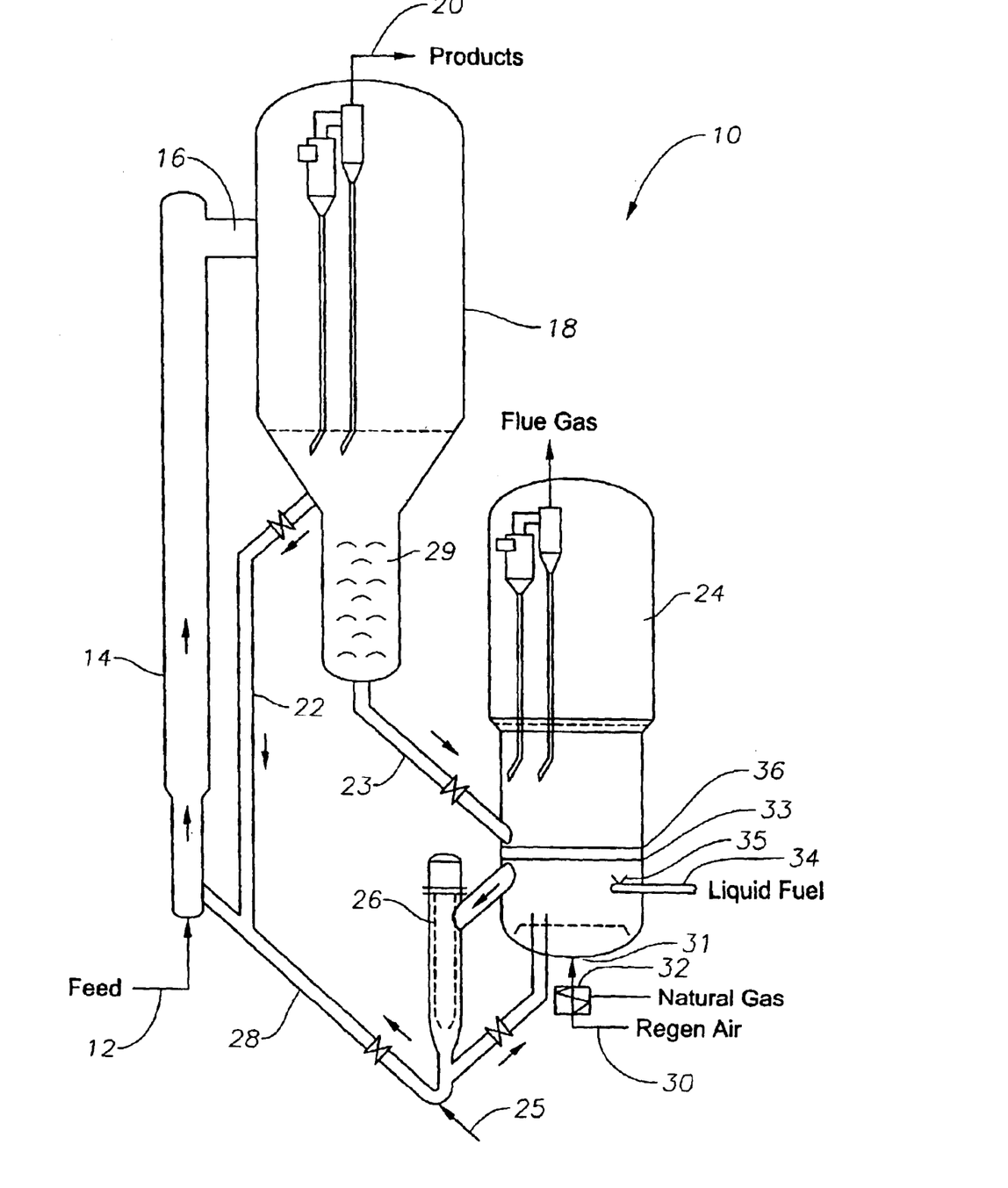

If the fluidized bed reactor is designed with low superficial gas velocities, below about 2 m/sec, then cyclones alone can be used to return catalyst fines to the fluidized bed reaction zone. Such reactors generally have high recirculation rates of solids within the fluidized bed, which allows the coke level on the catalyst to build to a preferred level. Similarly, in one embodiment, a regenerator will operate with a gas superficial velocity of or below about 2 m/s, preferably greater than about 1 m/s. A preferred embodiment of a reactor apparatus comprising a riser for use in the present invention is depicted generally as 10 in the FIGURE. A methanol feed 12 is at least partially vaporized in a preheater (not shown). The methanol feed is mixed with regenerated catalyst 28 and coked catalyst 22 at the bottom of the riser reactor 14. An inert gas and/or steam can be used to dilute the methanol, lift the catalyst streams 22 and 28, and keep pressure instrument lines clear of catalyst. This inert gas and/or steam mixes with the methanol and catalyst in the reactor 14. The reaction is exothermic, and a preferred reaction temperature, in the range of from about 300° C. to about 500° C., is maintained by removing heat. Heat can be removed by any suitable means, including but not necessarily limited to cooling the reactor with a catalyst cooler (not shown), feeding some of the methanol as a liquid, cooling the catalyst feed to the reactor, or any combination of these methods.

The reactor effluent 16, containing products, coked catalyst, diluents, and unconverted feed, should flow to a disengaging zone 18. In the disengaging zone 18, coked catalyst is separated from the gaseous materials by means of gravity and/or cyclone separators. A portion of the coked catalyst 22 is returned to the reactor inlet. The portion of coked catalyst 22 to be regenerated is first sent to a stripping zone 29, where steam or other inert gas is used to recover adsorbed hydrocarbons from the catalyst. Stripped spent coked catalyst 23 should flow to the regenerator 24. The portion of the catalyst sent to the regenerator 24 should be contacted with a regeneration medium, preferably a gas comprising oxygen, e.g., air, 30 introduced through regeneration medium inlet 31, at temperatures, pressures, and residence times that are capable of burning coke off of the catalyst and down to a level of less than about 0.5 wt %. The preferred temperature in the regenerator is in the range of from about 550° C. to about 725° C., a preferred oxygen concentration in the gas leaving the regenerator is in the range of from about 0.1 vol % to about 5 vol %, and a preferred catalyst residence time is in the range of from about 1 to about 100 minutes.

The burning off of coke is exothermic. The temperature can be maintained at a suitable level by any acceptable method, including but not limited to feeding cooler gas, cooling the catalyst in the regenerator with a cat cooler 26, or a combination of these methods.

The regenerated catalyst 28 is sent to the reactor 14, where it mixes with the recirculated coked catalyst 22 and the methanol feed 12. The regenerated catalyst 28 can be lifted to the reactor 14 by means of an inert gas, steam, or methanol vapor introduced via lift gas line 25. The process should repeat itself in a continuous or semi-continuous manner. The hot reactor product gases 20 should be cooled, the water byproduct condensed and collected, and the desired olefin product gases recovered for further processing.

In order to determine the level of coke in the reactor and in the regenerator, small samples of catalyst periodically can be withdrawn from various points in the recirculating system for measurement of carbon content. The reaction parameters can be adjusted accordingly.

As noted above, there are certain situations where it is desirable to add supplemental heat to the reactor/regenerator system. When starting from at or near ambient temperature, the regeneration zone 24 is initially heated with hot air, by combusting a gaseous or liquid starting fuel in auxiliary burner 32 with regeneration medium 30 introduced through regeneration medium (air) inlet 31. In one embodiment, the combustion occurs at or upstream of the regeneration medium inlet. As long as there is sufficient catalyst, say, up to a level 33, in the regeneration zone 24 to cover the heating fuel inlet 34, and provided that the temperature in zone 24 is above the autoignition temperature of the liquid fuel, then the heating fuel, e.g., a normally liquid fuel, can be injected into the regeneration zone 24 through one or more nozzles 35. The liquid heating fuel will react with the air, thereby adding heat to the regenerator.

In one embodiment, a second, less dense fluidized portion of the catalyst is maintained between level 33 and level 36 of the regeneration zone 24.

When the regenerator zone 24 is already above the autoignition temperature of the heating fuel, the heating fuel can be introduced without first using the auxiliary burner 32.

The flow rate of heating fuel can be varied according to the amount of heat required to bring the temperature of the catalyst and reactants to a temperature capable of initiating and sustaining the oxygenate conversion. Heated catalyst can be circulated within plural risers simultaneously, if necessary, to effect rapid start-up.

The heating fuel employed for the present invention exhibits certain properties. It must be clean with low, if any, sulfur, nitrogen or metal compound impurities. Typically, such impurities are individually present in amounts by weight of less than 100 wppm, 10 wppm, 1 wppm, or even less than 0.5 wppm. Additionally, such heating fuel exhibits a low autoignition temperature, typically, no greater than 371° C. (700° F.), e.g. 232° to 271° C. (450° to 520° F.). These temperatures can be reached in the regenerator zone 24 by operating the auxiliary burner 32 alone. In order to avoid the formation of localized "hot spots" within the reactor apparatus, the heating fuel has a molecular weight of at least 150, say at least 170, in order to promote a slow burn during combustion. The heating fuel can be a torch oil having the properties noted above.

Paraffins having the properties described above and ranging from 12 to 20 carbons are especially suited to use as the heating fuels used in the present invention and are preferably normally liquid, i.e., liquid under ambient conditions, say, room temperature and atmospheric pressure.

A preferred embodiment employs as a heating fuel $C_{12}$ to $C_{20}$ linear or normal paraffins. Especially preferred are liquid fuels which are prepared by treating a distillation cut by molecular exclusion chromatography to provide a product rich in normal paraffins. Such materials are available from ExxonMobil Chemical of Houston, Tex. under the name Norpar®. Norpar® fluids all have a flash point above 140° F. and are normal paraffins which have been isolated from kerosene. Norpar® 12 and Norpar® 14 are especially suited to use in the present invention. The number refers to the average carbon number of the material.

Another preferred embodiment employs as a heating fuel $C_{12}$ to $C_{20}$ branched paraffins. Such materials are available from ExxonMobil Chemical under the name Isopar®. Isopar® 12 (containing $C_{12}$ hydrocarbons) and Isopar® 14 (containing $C_{14}$ hydrocarbons) are especially suited to use in the present invention. The number refers to the average carbon number of the material.

Still another preferred embodiment employs as a heating fuel dearomatized aliphatic fluids available from ExxonMobil Chemical, such as Exxsol® D80 (containing $C_{12}$–$C_{13}$ hydrocarbons), Exxsol® D100 (containing $C_{13}$–$C_{14}$ hydrocarbons), Exxsol® D110 (containing $C_{14}$–$C_{16}$ hydrocarbons), Exxsol® D120 (containing $C_{14}$–$C_{18}$ hydrocarbons) and Exxsol® D140 (containing $C_{16}$–$C_{19}$ hydrocarbons).

Persons of ordinary skill in the art will recognize that many modifications can be made to the present invention without departing from the spirit and scope of the present invention. The embodiments described herein are meant to be illustrative only and should not be taken as limiting the invention, which is defined by the following claims.

What is claimed is:

1. A process for making an olefin product from an oxygenate feedstock in the presence of an oxygenate to olefin molecular sieve catalyst which comprises:
    a) contacting at least a portion of the catalyst with a regeneration medium in a regeneration zone;
    b) heating said regeneration zone to a first temperature of at least 225° C. (437° F.),
    c) feeding to said regeneration zone a heating fuel having an autoignition temperature less than the first temperature and containing less than 500 wppm sulfur and less than 200 wppm nitrogen, thereby causing the heating fuel to ignite and provide a heated catalyst;
    d) circulating said heated catalyst to the reaction zone; and
    e) additionally contacting the feedstock in a reaction zone with said oxygenate to olefin molecular sieve catalyst including said heated catalyst, under conditions effective to convert the feedstock into an olefin product stream.

2. The process of claim 1 wherein the olefin product stream comprises $C_2$–$C_3$ olefins.

3. The process of claim 1 wherein the conditions are further effective to form carbonaceous deposits onto catalyst.

4. The process of claim 1 wherein said catalyst is heated to at least 316° C. (600° F.) in the regeneration zone prior to the step of feeding the heating fuel.

5. The process of claim 1 wherein the regeneration zone has a fuel inlet and an air inlet capable of providing an airflow through said regeneration zone, located upstream from said fuel inlet in relation to direction of said airflow, and the process further comprises (1) combusting a starting fuel with an air stream from said air inlet thereby imparting sufficient heat content within said regeneration zone to obtain said first temperature at or near the fuel inlet and (2) feeding the heating fuel through said fuel inlet.

6. The process of claim 5 wherein said starting fuel comprises natural gas.

7. The process of claim 5 wherein said starting fuel has an autoignition temperature of greater than about 482° C. (90° F.).

8. The process of claim 5 which further comprises filling the regeneration zone with said catalyst to a level sufficient to cover said fuel inlet before the combusting step (1), and adding additional catalyst after step (2) of feeding the heating fuel, to provide additional heated catalyst.

9. The process of claim 5 wherein the catalyst is heated to at least 316° C. (600° F.) in the regeneration zone prior to the feeding step (2).

10. The process of claim 8 wherein the additional catalyst is heated to at least 316° C. (600° F.).

11. The process of claim 1 wherein the heating fuel is a liquid fuel which contains less than 100 wppm S and less than 100 wppm N.

12. The process of claim 1 wherein at least 50 wt % of said heating fuel is a $C_{11}$–$C_{20}$ hydrocarbon fraction.

13. The process of claim 1, wherein at least 75 wt % of said heating fuel is a $C_{11}$–$C_{20}$ hydrocarbon fraction.

14. The process of claim 1, wherein at least 85 wt % of said heating fuel is a $C_{11}$–$C_{20}$ hydrocarbon fraction.

15. The process of claim 1, wherein at least 75 wt % of said heating fuel is a $C_{12}$–$C_{19}$ hydrocarbon fraction and further said heating fuel has an autoignition temperature ranging from 232°–271° C. (450°–520° F.) and contains less than 10 wppm sulfur and less than 10 wppm nitrogen.

16. The process of claim 1, wherein at least 75 wt % of said heating fuel is a $C_{12}$ to $C_{16}$ hydrocarbon fraction.

17. The process of claim 1, wherein at least 75 wt % of the heating fuel is a $C_{12}$ to $C_{14}$ hydrocarbon fraction.

18. The process of claim 1, wherein said reaction zone comprises a riser.

19. The process of claim 1, wherein said reaction zone comprises plural risers.

20. The process of claim 1, wherein said reaction zone has two risers.

21. The process of claim 1, wherein said catalyst comprises molecular sieve having a pore diameter of less than 5.0 Angstroms.

22. The process of claim 21, wherein the catalyst comprises at least one molecular sieve framework-type selected from the group consisting of AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, and THO.

23. The process of claim 21, wherein the catalyst comprises at least one molecular sieve selected from the group consisting of ZSM-5, ZSM-4, SAPO-34, SAPO-17, SAPO-18, MCM-2, MeAPSO and substituted groups thereof.

24. The process of claim 1, wherein the catalyst comprises a molecular sieve having a pore diameter of 5–10 Angstroms.

25. The process of claim 24, wherein the catalyst comprises at least one molecular sieve framework-type selected from the group consisting of MFI, MEL, MTW, EUO, MTT, HEU, FER, AFO, AEL, TON, and substituted groups thereof.

26. The process of claim 1, wherein the heating step (b) occurs before the contacting step (c).

27. The process of claim 1, wherein the heating step (b) occurs concurrently with the contacting step (c).

28. The process of claim 1, wherein first contacting step (a) occurs before the heating step (b).

29. The process of claim 1, wherein said heating fuel contains less than 10 wppm sulfur and less than 10 wppm nitrogen.

30. A process for making an olefin product from oxygenate, comprising the steps of:
   a) heating a molecular sieve catalyst in a regeneration zone w a temperature of at least 225° C.;
   b) adding a heating fuel to the regeneration zone, wherein the heating fuel has an autoignition temperature less than the temperature of the heated catalyst in the regeneration zone, contains less than 500 wppm sulfa, and contains less than 200 wppm nitrogen;
   c) sending the catalyst from the regeneration zone to a reaction zone; and
   d) contacting the catalyst in the reaction zone with the oxygenate to form the olefin product.

31. The process of claim 30, wherein the heating fuel is added into a fluidized bed of the catalyst in the regeneration zone.

32. The process of claim 30, wherein the autoignition temperature of the heating fuel is not greater than 454° C.

33. The process of claim 30, wherein the autoignition temperature of the heating fuel is from 232°–271° C.

34. The process of claim 30, wherein the heating fuel contains metal in an amount of no greater than 100 wppm total metal.

35. The process of claim 30, wherein the catalyst is heated to at least 316° C. in the regeneration zone prior to adding the heating fuel.

36. The process of claim 30, wherein the catalyst is heated in step a) by combusting a starting fuel.

37. The process of claim 36, wherein the starting fuel is a gaseous carbonaceous fuel.

38. The process of claim 30, wherein the heating fuel is a liquid heating fuel.

39. The process of claim 30, wherein the heating fuel contains less than 100 wppm sulfur and less than 100 wppm nitrogen.

40. The process of claim 30, wherein the molecular sieve catalyst comprises molecular sieve having a pore diameter of less than 5 Angstroms.

41. The process of claim 30, wherein the molecular sieve catalyst comprises molecular sieve selected from the group consisting of ZSM-5, ZSM-4, SAPO-34, SAPO-17, SAPO-18, MCM-2, MeAPSO and substituted groups thereof.

* * * * *